US008116474B2

(12) United States Patent
Gierl et al.

(10) Patent No.: US 8,116,474 B2
(45) Date of Patent: Feb. 14, 2012

(54) SYSTEM FOR SUPPRESSING AMBIENT NOISE IN A HANDS-FREE DEVICE

(75) Inventors: Stefan Gierl, Karlsruhe (DE); Christoph Benz, Ohlsbach (DE)

(73) Assignee: Harman Becker Automotive Systems GmbH, Karlsbad (DE)

( * ) Notice: Subject to any disclaimer, the term of this patent is extended or adjusted under 35 U.S.C. 154(b) by 715 days.

(21) Appl. No.: 11/966,198

(22) Filed: Dec. 28, 2007

(65) Prior Publication Data

US 2008/0170708 A1 Jul. 17, 2008

Related U.S. Application Data

(63) Continuation of application No. 10/497,748, filed on Feb. 9, 2005, now Pat. No. 7,315,623.

(30) Foreign Application Priority Data

Dec. 4, 2001 (DE) .................................. 101 59 281

(51) Int. Cl.
*A61F 11/06* (2006.01)

(52) U.S. Cl. ..................................... 381/71.12; 704/210

(58) Field of Classification Search ...... 381/71.1–71.14, 381/93, 83, 94.1–94.9, 92; 455/501; 704/226, 704/210

See application file for complete search history.

(56) References Cited

U.S. PATENT DOCUMENTS 5,400,409 A * 3/1995 Linhard .......................... 381/92
5,539,859 A * 7/1996 Robbe et al. .................. 704/233
5,742,927 A * 4/1998 Crozier et al. ................ 704/226
5,943,429 A * 8/1999 Handel ........................ 381/94.2
6,339,758 B1 1/2002 Kanazawa et al.
6,463,408 B1 * 10/2002 Krasny et al. ................. 704/217
6,717,991 B1 * 4/2004 Gustafsson et al. .......... 375/285
7,315,623 B2 * 1/2008 Gierl et al. ................. 381/71.12
2002/0193130 A1 12/2002 Yang et al.
2003/0027600 A1 * 2/2003 Krasny et al. ................. 455/564
2003/0040908 A1 * 2/2003 Yang et al. ..................... 704/233
2003/0086575 A1 * 5/2003 Balan et al. .................. 381/94.2

FOREIGN PATENT DOCUMENTS

DE 19818608 * 10/1999

* cited by examiner

*Primary Examiner* — Xu Mei
*Assistant Examiner* — Lun-See Lao
(74) *Attorney, Agent, or Firm* — O'Shea Getz P.C.

(57) ABSTRACT

In order to suppress as much noise as possible in a hands-free device in a motor vehicle, for example, two microphones (M1, M2) are spaced a certain distance apart, the output signals (MS1, MS2) of which are added in an adder (AD) and subtracted in a subtracter (SU). The sum signal (S) of the adder (AD) undergoes a Fourier transform in a first Fourier transformer (F1), and the difference signal (D) of the subtracter (SU) undergoes a Fourier transform in a second Fourier transformer (F2). From the two Fourier transforms R(f) and D(f), a speech pause detector (P) detects speech pauses, during which a third arithmetic unit (R) calculates the transfer function $H_T$ of an adaptive transformation filter (TF). The transfer function of a spectral subtraction filter (SF), at the input of which the Fourier transform R(f) of the sum signal (S) is applied, is generated from the spectral power density $S_{rr}$ of the sum signal (S) and from the interference power density $S_{nn}$ generated by the adaptive transformation filter (TF). The output of the spectral subtraction filter (SF) is connected to the input of an inverse Fourier transformer (IF), at the output of which an audio signal (A) can be picked up in the time domain which is essentially free of ambient noise.

16 Claims, 1 Drawing Sheet

SYSTEM FOR SUPPRESSING AMBIENT NOISE IN A HANDS-FREE DEVICE

CLAIM OF PRIORITY

This patent application is a continuation of U.S. patent application Ser. No. 10/497,748 filed Feb. 9, 2005 now U.S. Pat. No. 7,315,623, which is hereby incorporated by reference.

FIELD OF THE INVENTION

The invention relates to suppressing ambient noise in a hands-free device having two microphones spaced a predetermined distance apart.

RELATED ART

Ambient noise represents a significant interference factor for the use of hands-free devices, which interference factor can significantly degrade the intelligibility of speech. Car phones are equipped with hands-free devices to allow the driver to concentrate fully on driving the vehicle and on traffic. However, particularly loud and interfering ambient noise is encountered in a vehicle.

There is a need for a technique of suppressing ambient noise for a hands-free device.

SUMMARY

A hands-free device is equipped with two microphones spaced a predetermined distance apart. The distance selected for the speaker relative to the microphones is smaller than the so-called diffuse-field distance, so that the direct sound components from the speaker at the location of the microphones predominate over the reflective components occurring within the space.

From the microphone signals supplied by the microphones, the sum and difference signal is generated from which the Fourier transform of the sum signal and the Fourier transform of the difference signal are generated.

From these Fourier transforms, the speech pauses are detected, for example, by determining their average short-term power levels. During speech pauses, the short-term power levels of the sum and difference signal are approximately equal, since for uncorrelated signal components it is unimportant whether these are added or subtracted before the calculation of power, whereas, based on the strongly correlated speech component, when speech begins the short-term power within the sum signal rises significantly relative to the short-term power in the difference signal. This rise is easily detected and exploited to reliably detect a speech pause. As a result, a speech pause can be detected with great reliability even in the case of loud ambient noise.

The spectral power density is determined from the Fourier transform of the sum signal and from the Fourier transform of the difference signal, from which the transfer function for an adaptive transformation filter is calculated. By multiplying the power density of the Fourier transform of the difference signal by its transfer function, this adaptive transformation filter generates the interference power density. From the spectral power density of the Fourier transform of the sum signal and from the interference power density generated by the adaptive transformation filter, the transfer function of an analogous adaptive spectral subtraction filter is calculated that filters the Fourier transform of the sum signal and supplies an audio signal essentially free of ambient noise at its output in the frequency domain, which signal is transformed back to the time domain using an inverse Fourier transform. At the output of this inverse Fourier transform, an audio or speech signal essentially free of ambient noise can be picked up in the time domain and then processed further.

These and other objects, features and advantages of the present invention will become more apparent in light of the following detailed description of preferred embodiments thereof, as illustrated in the accompanying drawing.

DESCRIPTION OF THE DRAWING

The FIGURE is a block diagram illustration of a device for suppressing ambient noise in a hands-free device.

DETAILED DESCRIPTION

Figure 1:
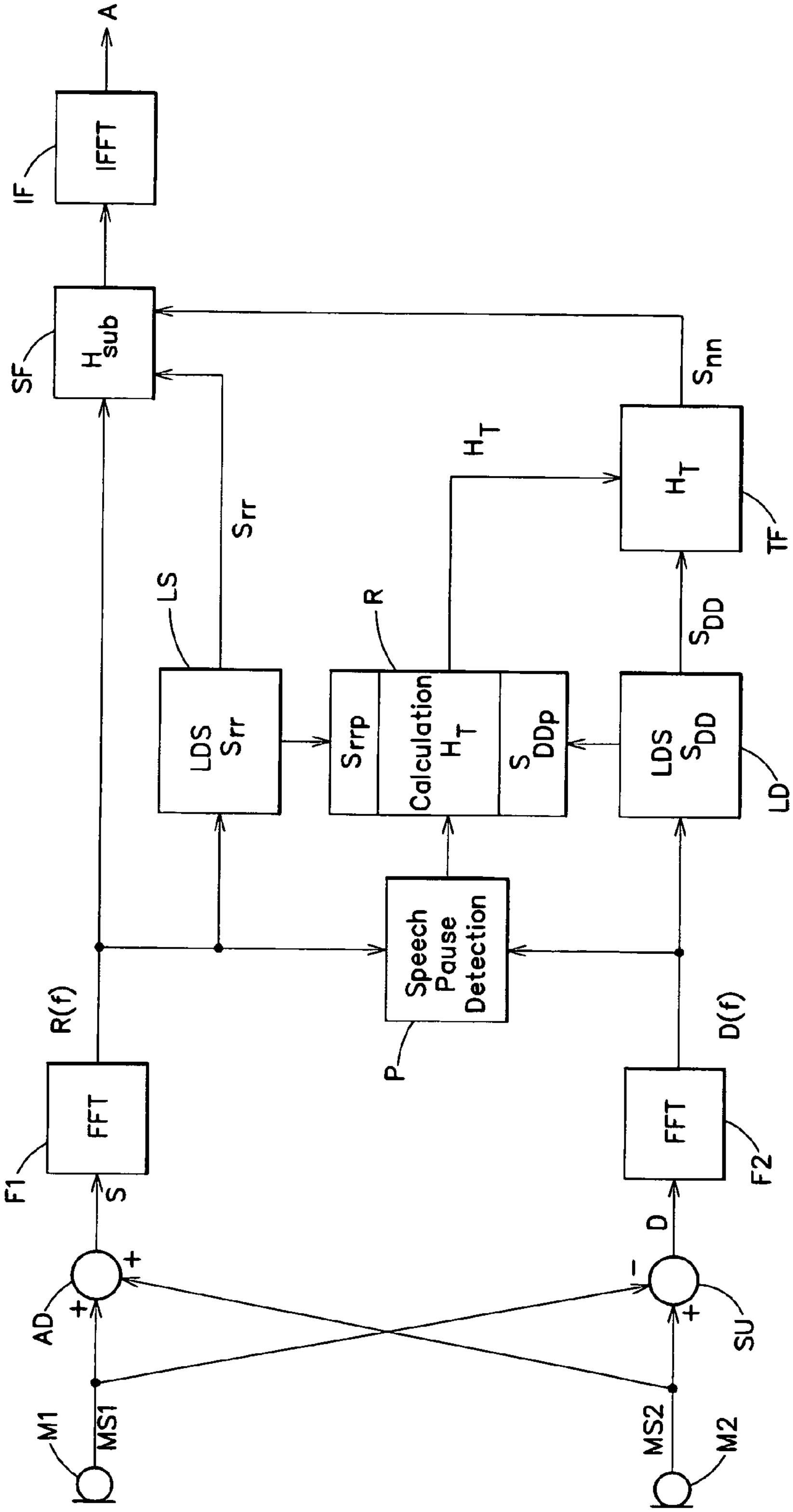

The output of a first microphone 100 is provided on a line 102 to an adder 104 and a subtracter 106, while a second microphone 108 provides a sensed signal on a line 110 to the adder 104 and the subtracter 106. The adder 104 provides an output on a line 112 to a first Fourier transformer 114, the output of which on a line 116 is input to a speech pause detector 118, to a first arithmetic unit 120 to calculate the spectral power density $S_{rr}$ of the Fourier transform R(f) of the sum signal, and to an adaptive spectral subtraction filter 122.

The subtracter 106 provides a difference signal on line 124 to a second Fourier transformer 126, the output of which on a line 128 is connected to the speech pause detector 118 and to a second arithmetic unit 130 to calculate the spectral power density $S_{DD}$ of the Fourier transform D(f) of the difference signal on the line 124. The first arithmetic unit 120 provides an output on a line 129 to a third arithmetic unit 132 to calculate the transfer function of an adaptive transformation filter 140, and to the adaptive spectral subtraction filter 122, the output of which is connected to an inverse Fourier transformer 160. The second arithmetic unit 130 provides a signal on line 133, indicative of the spectral power density $S_{DD}$, to the third arithmetic unit 132, and to an adaptive transformation filter 140, the output of which is connected to the adaptive spectral subtraction filter 122. The output of the speech pause detector 118 is also connected to the third arithmetic unit 132, that provides an output which is connected to the control input of the adaptive transformation filter 140.

As mentioned above, the two microphones 100 and 108 are separated a distance which is smaller than the so-called diffuse-field distance. For this reason, the direct sound components of the speaker predominate at the site of the microphone over the reflection components occurring within a closed space, such as the interior of a vehicle.

The short-term power of the Fourier transform R(f) on the line 116 of the sum signal and of the Fourier transform D(f) on the line 128 of the difference signal is determined in the speech pause detector 118. During pauses in speech, the two short-term power levels differ hardly at all since it is unimportant for the uncorrelated speech components whether they are added or subtracted before the power calculation. When speech begins, on the other hand, the short-term power within the sum signal rises significantly relative to the short-term power in the difference signal due to the strongly correlated speech component. This rise thus indicates the end of a speech pause and the beginning of speech.

The first arithmetic unit 120 uses time averaging to calculate the spectral power density $S_{rr}$ of the Fourier transform R(f) on the line 116. Similarly, the second arithmetic unit 130 calculates the spectral power density $S_{DD}$ of the Fourier transform D(f) on the line 128. From the power density $S_{rrp}(f)$ and the spectral power density $S_{DDp}(f)$ during the speech pauses, the third arithmetic unit 132 calculates the transfer function $H_T(f)$ of the adaptive transformation filter 140 using the following equation:

$$H_T(f)=S_{rrp}(f)/S_{DDp}(f) \quad (1)$$

Preferably, an additional time averaging—that is, a smoothing—of the coefficients of the transfer function thus obtained is used to significantly improve the suppression of ambient noise by preventing the occurrence of so-called artifacts, often called "musical tones."

The spectral power density $S_{rr}(f)$ is obtained from the Fourier transform R(f) of the sum signal on the line 116 by time averaging, while in analogous fashion the spectral power density $S_{DD}(f)$ is calculated by time averaging from the Fourier transform D(f) of the difference signal on the line 128.

For example, the spectral power density $S_{rr}$ is calculated using the following equation (2):

$$S_{rr}(f,k)=c*|R(f)|^2+(1-c)*S_{rr}(f,k-1) \quad (2)$$

In analogous fashion, the spectral power density $S_{DD}(f)$ is, for example, calculated using the equation (3):

$$S_{DD}(f,k)=c*|D(f)|^2+(1-c)*S_{DD}(f,k-1) \quad (3)$$

The term c is a constant between 0 and 1 which determines the averaging time period. When c=1, no time averaging takes place; instead the absolute squares of the Fourier transforms R(f) and D(f) are taken as the estimates for the spectral power densities. The calculation of the residual spectral power densities required to implement the method according to the invention is preferably performed in the same manner.

The adaptive transformation filter 140 uses its transfer function $H_T(f)$ to generate the interference power density $S_{nn}$ on line 152 from the spectral power density $S_{DD}(f)$ on the line 154 using the following equation (4):

$$S_{nn}(f)=H_T*S_{DD}(f) \quad (4)$$

Using the interference power density $S_{nn}$ on the line 152 and the spectral power density $S_{rr}$ on the line 156 the transfer function $H_{sub}$ of the spectral subtraction filter 122 is calculated as specified by equation (5):

$$H_{sub}(f)=1-a*S_{nn}(f)/S_{rr}(f) \text{ for } 1-a*S_{nn}(f)/S_{rr}(f)>b$$

$$H_{sub}(f)=b \text{ for } 1-a*S(f)/S_{rr}(f)\leqq b$$

The parameter a represents the so-called overestimate factor, while b represents the so-called "spectral floor."

The interference components picked up by the microphones 100 and 108, which strike the microphones as diffuse sound waves, can be viewed as virtually uncorrelated for almost the entire frequency range of interest. However, there does exist for low frequencies a certain correlation dependent on the relative spacing of the two microphones, which correlation results in the interference components contained in the reference signal appearing to be high-pass-filtered to a certain extent. In order to prevent a faulty estimation of the low-frequency interference components in the spectral subtraction, a spectral boost of the low-frequency components of the reference signal is performed by the adaptive transformation filter 140.

The method according to the invention and the hands-free device according to the invention, which are particularly suitable for a car phone, are distinguished by excellent speech quality and intelligibility since the estimated value for the interference power density $S_{nn}$ on the line 152 is continuously updated independently of the speech activity. As a result, the transfer function of the spectral subtraction filter 122 is also continuously updated, both during speech activity and during speech pauses. As was mentioned above, speech pauses are detected reliably and precisely, this detection being necessary to update the transformation filter 140.

The audio signal at the output on line 158 of the spectral subtraction filter 122, which signal is essentially free of ambient noise, is fed to the inverse Fourier transformer 160 which transforms the audio signal back to the time domain.

Although the present invention has been illustrated and described with respect to several preferred embodiments thereof, various changes, omissions and additions to the form and detail thereof, may be made therein, without departing from the spirit and scope of the invention.

What is claimed is:

1. A noise reduction system, comprising:

an adder that sums first and second input audio signals to provide a sum signal;

a subtractor that subtracts the first input audio signal from the second input audio signal to provide a difference signal;

a speech pause detector that compares the sum and the difference signals to generate a speech pause signal;

first and second arithmetic units, each of which respectively determines a spectral power density of the sum signal or the difference signal;

an adaptive transformation filter that processes the spectral power density of the difference signal, as a function of the speech pause signal, to estimate an interference power density; and an adaptive spectral subtraction filter that filters the sum signal, as a function of the spectral power density of the sum signal and the interference power density, to provide a filtered output signal.

2. The system of claim 1, further comprising first and second microphones, where first microphone generates the first input audio signal, and where the second microphone generates the second input audio signal.

3. The system of claim 1, further comprising:

a first time-to-frequency domain transformation unit that receives the sum signal in a time domain, and provides the sum signal to the speech pause detector, the first arithmetic unit and the adaptive spectral subtraction filter in a frequency domain; and a second time-to-frequency domain transformation unit that receives the difference signal in the time domain, and provides the difference signal to the speech pause detector and the second arithmetic unit in the frequency domain.

4. The system of claim 3, further comprising a frequency-to-time domain transformation unit that provides the filtered output signal in a time domain.

5. The system of claim 1, further comprising a third arithmetic unit that processes the spectral power densities of the sum and the difference signals, as a function of the speech pause signal, to update a transfer function $H_T$ of the adaptive transformation filter.

6. The system of claim 1, where the speech pause detector compares the sum and the difference signals by comparing short-term power levels of the sum and the difference signals.

7. The system of claim 1, where the first and the second arithmetic units use time averaging to determine the spectral power densities of the sum and the difference signals.

8. A method for reducing signal noise, comprising:

processing first and second input audio signals to provide sum and difference signals;

detecting a speech pause by comparing the sum and the difference signals;

respectively determining spectral power densities of the sum and the difference signals;

processing the spectral power density of the difference signal, as a function of the speech pause signal, to estimate an interference power density; and reducing signal noise in the sum signal with an adaptive filter, as a function of the spectral power density of the sum signal and the interference power density, to provide an audio signal.

9. The method of claim 8, where the processing the first and the second input audio signals comprises:

summing first and second input audio signals to provide the sum signal; and subtracting the first input audio signal from the second input audio signal to provide the difference signal.

10. The method of claim 8, where the signal noise is reduced in the sum signal to suppress ambient noise for a hands-free device.

11. The method of claim 8, further comprising respectively generating the first and the second input audio signals with first and second microphones.

12. The method of claim 8, where the processing of the first and the second input audio signals is performed in a time domain; and the detecting of the speech pause, the determining of the spectral densities, the adaptively processing of the spectral power density of the difference signal, and the reducing of the signal noise are performed in a frequency domain.

13. The method of claim 12, further comprising transforming the audio signal from the frequency domain to the time domain.

14. The method of claim 8, further comprising processing the spectral power densities of the sum and the difference signals, as a function of the speech pause signal, to update a transfer function $H_T$ of a transformation filter, where the interference power density is estimated using the transformation filter with the updated transfer function $H_T$.

15. The method of claim 8, where the comparing of the sum and the difference signals comprises comparing a difference between short-term power levels of the sum and the difference signals.

16. The method of claim 8, where the spectral power densities of the sum and the difference signals are determined using time averaging.

* * * * *